US006994799B2

(12) United States Patent  (10) Patent No.: US 6,994,799 B2
Van Driessche et al.  (45) Date of Patent: Feb. 7, 2006

(54) ESTER-CONTAINING FLUID COMPOSITIONS

(75) Inventors: Eddy Van Driessche, Eeklo (BE); Georges Mathys, Korbeek-Lo (BE); Richard H. Schlosberg, Bridgewater, NJ (US); Christian Francois, Ottenburg (BE); Chris De Roover, Beerse (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 339 days.

(21) Appl. No.: 09/747,146

(22) Filed: Dec. 22, 2000

(65) Prior Publication Data

US 2002/0005503 A1 Jan. 17, 2002

Related U.S. Application Data

(60) Provisional application No. 60/173,500, filed on Dec. 29, 1999.

(51) Int. Cl.
*C09K 5/00* (2006.01)

(52) U.S. Cl. ............................. 252/71; 252/70; 252/73; 252/570; 252/578; 252/579

(58) Field of Classification Search ................. 252/70, 252/71, 73, 570, 578, 579
See application file for complete search history.

(56) References Cited

U.S. PATENT DOCUMENTS

| 3,700,706 | A |   | 10/1972 | Butter ................. 260/410.9 R |
|---|---|---|---|---|
| 3,832,391 | A |   | 8/1974 | Parshall ..................... 260/497 |
| 3,906,016 | A |   | 9/1975 | Isa et al. .............. 260/410.9 R |
| 4,158,668 | A |   | 6/1979 | Morris ....................... 260/413 |
| 4,258,206 | A |   | 3/1981 | Pittman, Jr. et al. ........ 560/233 |
| 4,303,589 | A |   | 12/1981 | Chen ................... 260/410.9 R |
| 4,414,409 | A |   | 11/1983 | Waller ........................ 560/233 |
| 4,427,593 | A |   | 1/1984 | Hofmann et al. ..... 260/410.9 R |
| 4,578,367 | A |   | 3/1986 | Hofmann ..................... 502/24 |
| 5,185,092 | A |   | 2/1993 | Fukuda et al. ................ 252/56 |
| 5,405,720 | A |   | 4/1995 | Hosaka et al. .............. 430/191 |
| 5,681,800 | A | * | 10/1997 | Duncan et al. ............. 508/485 |
| 5,969,205 | A |   | 10/1999 | Stüwe et al. ................ 585/664 |

FOREIGN PATENT DOCUMENTS

| WO | WO97/27167 | 7/1997 |
|---|---|---|
| WO | PCT/US99/09885 | 5/1999 |
| WO | WO99/57217 | 11/1999 |

OTHER PUBLICATIONS

Colquhoun, et al., *Carbonylation: Direct Synthesis of Carbonyl Compounds*, Section 7.3, Esters: From Alenes, pp. 119–129, Plenum Press, 1991.

*Kirk–Othmer Encyclopedia of Chemical Technology*, 4th Ed., vol. 24, pp. 456–490.

Picquet, et al., "Kinetics of the Reactions of OH Radicals with Some Oxygenated Volatile Organic Compounds under Simulated Atmospheric Conditions," *Inat. J. Chem. Kinet.*, 30, 839–847 (1998).

Bilde, et al, "Atmospheric Chemistry of Dimethyl Carbonate: Reaction with OH Radicals, UV Spectra of $CH_3OC(O)OCH_2$ and $CH_3OC(O)OCH_2O_2$ Radicals, Reactions of $CH_3OC(O)OCH_2O_2$ with NO and $NO_2$, and Fate of $CH_3OC(O)OCH_2O$ Radicals," *J. Phys. Chem. A*, 101, 3514–3525 (1997).

"Proposed Reactivity Adjustment Factors for Transitional Low Emissions Vehicles—Staff Report and Technical Support Document," California Air Resources Board, Sacramento, CA, Sep. 27, 1991.

Carter, William P.L., "Development and Evaluation of a Detailed Mechanism for the Atmospheric Reactions of Isoprene and NOx," *International Journal of Chemical Kinetics*, 28, 497–530 (1996).

Carter, William, P.L., "Computer Modeling of Environmental Chamber Measurements of Maximum Incremental Reactivities of Volatile Organic Compounds," *Atmospheric Environment*, 29, 2513–2527 (1995).

Carter, William, P.L., et al, "Environmental Chamber Study of Maximum Incremental Reactivities of Volatile Organic Compounds," *Atmospheric Environment*, 29, 2499–2511 (1995).

Carter, William, P.L., "Development of Ozone Reactivity Scales for Volatile Organic Compounds," *Journal of the Air and Waste Management Association*, 44, 881–889 (1994).

Carter, William, P.L., "Computer Modeling Study of Incremental Hydrocarbon Reactivity," *Environ, Sci. Technol.*, 23, 864 (1989).

Carter, William, P. L., *Preliminary Report to California Air Resources Board, Contract No. 95–308*, Aug. 6, 1998.
Http://helium.ucr.edu/~carter/index.html.
Http://www.cert.ucr.edu/~carter/r98tab.htm.
Http://helium.ucr.edu/~carter/sapric97.html.
Http://palimpsest.stanford.edu/byauth/burke/solpar/solpar6.html.

Archer, Wesley, *Industrial Solvents Handbook*, pp 35–68 and 297–309, Marcel Dekker (1996).

* cited by examiner

*Primary Examiner*—Derrick Hamlin
(74) *Attorney, Agent, or Firm*—Louis N. Moreno

(57) ABSTRACT

Disclosed are ester-containing fluid compositions, methods of making such compositions, and methods of using such compositions. The fluid compositions comprise a mix of branched and linear ester compounds, and the fluid compositions are characterized by certain performance limitations. The preferred method of making the fluid compositions enables the ester mix to be made in a one step process with little finishing required to obtain desirable performance characteristics.

24 Claims, No Drawings

ESTER-CONTAINING FLUID COMPOSITIONS

This application claim the benefit of Provisional Application No. 60/173,500, filed Dec. 29, 1999.

FIELD OF THE INVENTION

This invention is directed to ester-containing fluid compositions, methods of making such compositions, and methods of using such compositions. More specifically this invention is directed to fluid compositions which comprise certain ester compounds, and the fluid compositions is characterized by certain performance limitations.

BACKGROUND OF THE INVENTION

Formulations of hydrocarbon fluids for various uses are continuously being changed due to a variety of concerns. The major concerns warranting reformulations, however, are typically environmental or toxicological. That is, after a hydrocarbon fluid has been formulated for a desired end use, it is often found some time after commercialization that a component of the fluid or the entire fluid itself is no longer acceptable due to new environmental concerns or due to newly gathered data that tends to suggest that some hydrocarbon compound or formulation may be toxic or otherwise unsuitable in certain situations. For example, environmental concerns of contributions to stratospheric ozone depiction using the refrigerant R-12 led to the use of a new refrigerant R-134a. This change in refrigerant also led to completely new ester-containing formulations for use as lubricant fluids with the new R-134a refrigeration systems. See, for example, U.S. Pat. No. 5,185,092, now assigned to Exxon.

Reformulations have been required with regard to solvents for use with photoresists due to concerns of toxicity in photoresist compositions previously containing Cellosolve™ type solvents. Such compositions now tend to use relatively non-toxic ester solvents such as ethyl lactate and n-butyl acetate containing solvents, which are also low in particle formation. See, for example, U.S. Pat. No. 5,405,720.

As those of skill in the art readily appreciate, it is not an easy task to reformulate fluid compositions to meet the many performance characteristics that are required for numerous end uses. This is particularly a daunting task when the various alternative chemical compositions are expensive to make or are not available in the volumes needed for commercial use. It is, therefore, a continuing problem to find low cost fluid compositions that can be used to reformulate known hydrocarbon fluid compositions that have been found to now cause environmental or toxicological concerns. It is also a much greater problem to find low cost fluid compositions that can meet the various performance requirements required in numerous end uses.

SUMMARY OF THE INVENTION

This invention provides a solution to the continuing problems associated with reformulating hydrocarbon fluid compositions. According to the invention, fluid compositions are provided which comprise a mix of branched and linear ester compounds, with the fluid compositions exhibiting certain performance characteristics. The fluid compositions of the invention can be made at a low cost commercial scale by preferred processing components.

In a preferred embodiment, the invention provides a mix of certain branched and certain linear ester compounds. The mix of branched and linear ester compounds is defined as:

(a) a compound of formula I:

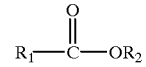

wherein $R_1$ is linear $C_3$–$C_6$ alkyl, and $R_2$ is $C_1$–$C_4$ alkyl; and (b) a compound of formula II:

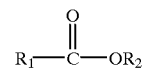

wherein $R_1$ is branched $C_3$–$C_6$ alkyl, and $R_2$ is $C_1$–$C_4$ alkyl; and $R_1$ of formula I and $R_1$ of formula II have an equal number of carbons, with formula I and formula II being present at a ratio of 2–100: 1. In other particular embodiments, the ratio of formula I to formula II is 3–50:1, preferably 3.5–40:1, more preferably 3.5–20:1.

The fluid compositions of this invention can also contain additional components. Desirable components include at least one additional compound selected from the group consisting of $C_6$–$C_9$ alkanes, $C_7^+$ aromatics, $C_1$–$C_9$ alcohols, $C_3$–$C_9$ ketones, $C_3$–$C_{12}$ esters, $C_3$–$C_{12}$ ethers, and $C_1$–$C_{12}$ halocarbons.

In another desirable embodiment the Maximum Incremental Reactivity (MIR) of the fluid compositions of this invention is less than or equal to 2.0 grams of ozone produced per gram of fluid composition, more preferably less than or equal to 1.5 gram of ozone produced per grain of fluid composition, and most preferably less than or equal to 1.0 gram of ozone produced per gram of fluid composition.

In yet another embodiment, the flash point of the composition of this invention is preferably at least 3° C. or higher, more preferably greater than 7° C., even more preferably greater than 14° C., still more preferably greater than 21° C.

It is convenient for the fluid of this invention to have an evaporation rate less than 12 times the evaporation rate of n-butyl acetate, preferably in a range of 0.1 to 12 relative to n-butyl acetate, and more preferably in a range of 0.5 to 8.

When used as a solvent, the fluid compositions of this invention preferably have Hansen Solubility Parameters of $\delta_d$ between about 13 to 20, $\delta_p$ of between about 2 to 10, and $\delta_h$ of between about 3 to 18.

In another desirable embodiment, the initial boiling point of the fluid of this invention is preferably at least about 60° C., more preferably at least about 70° C., most preferably at least about 80° C.

The fluid of this invention is desirably low in water and total acid content. It is particularly desirable that the fluid compositions have a moisture content of less than or equal to about 1.0 wt. %, more desirably 0.5 wt. %, even more desirably less than or equal to about 0.3 wt. %, most desirably less than or equal to about 0.1 wt. %. Desirably the fluid compositions of the invention have a total acid content of less than or equal to about 0.1 wt. %, more desirably less than or equal to about 0.05 wt. %, most desirably less than or equal to about 0.01 wt. %.

In another embodiment, the invention is to a fluid composition comprising:

(a) a compound of formula I:

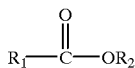

wherein $R_1$ is linear $C_3$–$C_6$ alkyl, and $R_2$ is $C_1$–$C_4$ alkyl;
(b) a compound of formula II:

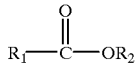

wherein $R_1$ is branched $C_3$–$C_6$ alkyl, and $R_2$ is $C_1$–$C_4$ alkyl; and $R_1$ of formula I and $R_1$ of formula II have an equal number of carbons, with formula I and formula II being present at a weight ratio of 2–100:1; and
(c) a compound of the formula III:

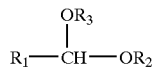

wherein $R_1$ is $C_3$–$C_6$ alkyl, $R_2$ is $C_1$–$C_4$ alkyl, and $R_3$ is $C_1$–$C_4$ alkyl. Desirably, the compound of formula III is present in the fluid composition at not greater than a concentration of about 5 wt. %, preferably about 0.01 wt. % to about 3 wt. %, more preferably about 0.05 wt. % to about 2 wt. %.

wherein $R_1$ is $C_3$–$C_6$ alkyl, $R_2$ is $C_1$–$C_4$ alkyl, and $R_3$ is $C_1$–$C_4$ alkyl.

In yet another embodiment, the invention provides a method of making a fluid composition comprising:

contacting a mixture of a raffinate-1 stream, CO, and a $C_1$–$C_4$ alcohol with a carbonylation catalyst under conditions effective to provide a composition containing (a) a compound of formula I:

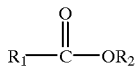

wherein $R_1$ is linear $C_3$–$C_6$ alkyl, and $R_2$ is $C_1$–$C_4$ alkyl;
(b) a compound of formula II:

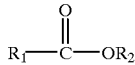

wherein $R_1$ is branched $C_3$–$C_6$ alkyl, and $R_2$ is $C_1$–$C_4$ alkyl; and $R_1$ of formula I and $R_1$ of formula II have an equal number of carbons, with formula I and formula II being present at a weight ratio of 2–100: 1; and
(c) a compound of the formula III:

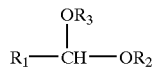

wherein $R_1$ is $C_3$–$C_6$ alkyl, $R_2$ is $C_1$–$C_4$ alkyl, and $R_3$ is $C_1$–$C_4$ alkyl.

DETAILED DESCRIPTION OF THE INVENTION

This invention is directed to ester-containing fluid compositions that exhibit a variety of desirable characteristics relative to a variety of end uses. Such characteristics are identified as ozone formation potential (OFP), flash point, Hansen Solubility Parameter, initial boiling point, evaporation rate, water content, total acid content, and low particle formation, each characteristic depending upon the desired use.

A central feature of the invention is that the fluid compositions are environmentally friendly. They contain a preferred mix of certain branched and certain linear ester compounds. The mix is particularly suitable for replacing compounds that have undesirable environmental characteristics. For example, the mix is particularly good for replacing butyl acetate for a wide variety of solvent compositions. The preferred mix of branched and linear ester compounds is defined as:

(a) a compound of formula I:

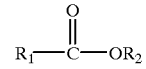

wherein $R_1$ is linear $C_3$–$C_6$ alkyl, and $R_2$ is $C_1$–$C_4$ alkyl; and
(b) a compound of formula II:

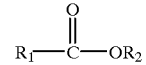

wherein $R_1$ is branched $C_3$–$C_6$ alkyl, and $R_2$ is $C_1$–$C_4$ alkyl; and $R_1$ of formula I and $R_1$ of formula II have an equal number of carbons, with formula I and formula II being present at a weight ratio of 2–100:1. In other particular embodiments, the weight ratio of formula I to formula II is 3–50:1, preferably 3.5–40:1, more preferably 3.5–20:1.

The total amount of the compound of formula I, as well as the compound of formula II present in the fluid compositions, can vary depending upon the desired characteristics required for use. Desirably the total amount of formula I present in the fluid compositions is at least 5 wt. %, more desirably at least 10 wt. %, most desirably at least 25 wt. %. In its preferred form, the fluid compositions will have a total amount of the compound of formula I of at least 50 wt. %, more preferably at least 70 wt. %, most preferably at least 80 wt. % so that it can be blended to a variety of end uses and modified to exhibit multiple desirable characteristics.

Representative compounds of formula I include methyl butanoate, ethyl butanoate, propyl butanoate, butyl butanoate, isopropyl butanoate, isobutyl butanoate, tert butyl butanoate, methyl pentanoate, ethyl pentanoate, propyl pentanoate, butyl pentanoate, isopropyl pentanoate, isobutyl pentanoate, tert butyl pentanoate, methyl hexanoate, ethyl hexanoate, propyl hexanoate, butyl hexanoate, isopropyl hexanoate, isobutyl hexanoate, tert butyl hexanoate, methyl heptanoate, ethyl heptanoate, propyl heptanoate, butyl heptanoate, isopropyl heptanoate, isobutyl heptanoate, tert butyl heptanoate, and combinations thereof. Preferred compounds are methyl, ethyl and isopropyl pentanoate, with the most preferred being methyl pentanoate.

Representative compounds of formula II include methyl 2-methyl propionate, ethyl 2-methyl propionate, propyl 2-methyl propionate, butyl 2-methyl propionate, isopropyl 2-methyl propionate, isobutyl 2-methyl propionate, tert butyl 2-methyl propionate, methyl 2-methyl butanoate, ethyl 2-methyl butanoate, propyl 2-methyl butanoate, butyl 2-methyl butanoate, isopropyl 2-methyl butanoate, isobutyl 2-methyl butanoate, tert butyl 2-methyl butanoate, methyl 2-methyl pentanoate, ethyl 2-methyl pentanoate, propyl 2-methyl pentanoate, butyl 2-methyl pentanoate, isopropyl 2-methyl pentanoate, isobutyl 2-methyl pentanoate, tert butyl 2-methyl pentanoate, and combinations thereof. Preferred compounds are methyl, ethyl, and isopropyl 2-methyl butanoate, with the most preferred being methyl 2-methyl butanoate.

When formula I and formula II are both present in the fluid compositions of this invention, $R_2$ of formula I and $R_2$ of formula II can be the same or different. Preferably, $R_2$ of formula I and formula II are the same. Preferred combinations of the compounds of formula I and formula II are methyl butanoate/methyl 2-methyl propionate, ethyl butanoate/ethyl 2-methyl propionate, propyl butanoate/propyl 2-methyl propionate, butyl butanoate/butyl 2-methyl propionate, isopropyl butanoate/isopropyl 2-methyl propionate, isobutyl butanoate/isobutyl 2-methyl propionate, tert butyl butanoate/tert butyl 2-methyl propionate, methyl pentanoate/methyl 2-methyl butanoate, ethyl pentanoate/ethyl 2-methyl butanoate, propyl pentanoate/propyl 2-methyl butanoate, butyl pentanoate/butyl 2-methyl butanoate, isopropyl pentanoate/Isopropyl 2-methyl butanoate, isobutyl pentanoate/isobutyl 2-methyl butanoate, tert butyl pentanoate/tert butyl 2-methyl butanoate, methyl hexanoate/methyl 2-methyl pentanoate, ethyl hexanoate/ethyl 2-methyl pentanoate, propyl hexanoate/propyl 2-methyl pentanoate, butyl hexanoate/butyl 2-methyl pentanoate, isopropyl hexanoate/isopropyl 2-methyl pentanoate, isobutyl hexanoate/isobutyl 2-methyl pentanoate, tert butyl hexanoate/tert butyl 2-methyl pentanoate. Preferred combinations are methyl pentanoate/methyl 2-methyl butanoate, ethyl pentanoate/ethyl 2-methyl butanoate, and isopropyl pentanoate/isopropyl 2-methyl butanoate, with the most preferred being methyl pentanoate/methyl 2-methyl butanoate.

Compounds of the formula I can be made separately from the compounds of the formula II and the compounds added together if desired. For example the appropriate alcohols can be reacted with the appropriate carboxylic acids to form the desired ester products. This type of esterification reaction is well known to those of ordinary skill in the art.

In a preferred embodiment, a combination of esters of formula I and formula II can be made in a one step process using a hydroesterification reaction. This process is described in greater detail in *Carbonylation: Direct Synthesis of Carbonyl Compounds*, Colquhoun, et al., Plenum Press, 1991, the pertinent portions of which are incorporated herein by reference. See, in particular, Chapter 7, in particular pages 1 19–129.

In the hydroesterification reaction used in this invention, a mixture of carbon monoxide (CO), an alcohol, and an alkene is contacted with a carbonylation catalyst under conditions effective to convert the mixture to an ester product. The reaction conditions employable in the processes of this invention are chosen depending on the particular syntheses desired. Such process conditions are well known in the art. All of the processes of this invention can be carried out in accordance with conventional procedures known in the art. Illustrative reaction conditions for conducting the processes of this invention are described, for example, in *Kirk-Othmer Encyclopedia of Chemical Technology*, Fourth Edition, 1996, the pertinent portions of which are incorporated herein by reference. Depending on the particular process, operating temperatures may range from about –80° C. to about 500° C. and operating pressures can range from about 1 psig to about 10,000 psig.

The processes of this invention are conducted for a period of time sufficient to produce the desired products. The exact reaction time employed is dependent, in part, upon factors such as temperature, pressure, nature and proportion of starting materials, and the like. The reaction time will normally be within the range of from about one-half to about 200 hours, and preferably from less than about one to about 10 hours.

The alcohols which can be used in the hydroesterification reaction of this invention are desirably $C_1$–$C_4$ alcohols. Such alcohols include methanol, ethanol, propanol, isopropanol n-butanol, isobutanol, tert butanol, and mixtures thereof. Methanol is most preferred.

The alkenes which can be used in the hydroesterification reaction of this invention are $C_3$–$C_6$ alkenes. The alkenes are preferably linear, although a mix containing branched alkenes can be used. In a preferred embodiment a dilute $C_4$ stream is used. In its more dilute form, raffinate-1 is used. Raffinate 1 is a composition comprising a mixture of butanes, n-butenes and isobutylene. A typical composition of a raffinate-1 stream from a steam cracker is: n-butane about 10–20 vol. %: i-butane about 0.5–1 vol. %; 1-butene about 20–25 vol. %; 2-butene (cis) about 5–8 vol. %; 2-butene (trans) about 8–11 vol. %; i-butene about 38–45 vol. %; butadiene about 0.1–0.3 vol. %; $C_3$ hydrocarbon about 0–1 vol. %; $C_5$ hydrocarbon about 0–1 vol. %. In a less dilute form, raffinate-2 is used. Raffinate-2 is a composition comprising a mixture of predominately butanes and n-butenes.

Raffinate-1 and raffinate-2 can be obtained from cracking processes where higher molecular weight hydrocarbons (e.g., gas oil or naphtha fractions) are thermally or catalytically broken down. Such processes conventionally produce a product containing primarily ethylene and propylene, with some production of other components generally known as a $C_4$ stream. After conventional separation of the ethylene and propylene, the $C_4$ stream contains predominantly butanes, n-butenes, isobutylene and butadiene. This stream is then hydrogenated to form a butadiene depleted stream known as raftinate-1. A subsequent step separates isobutylene from the raffinate-1 via reaction with methanol (to form MtBE) or via isobutylene dimerization to diisobutylene thereby producing the butane/linear butene stream known as raffinate-2. For a more detailed discussion on raffinate-1 and raffinate-2 streams, see U.S. Pat. No. 5,969,205, the details of which are incorporated herein by reference.

The catalyst used in the esterification reaction can be any conventional carbonylation type catalyst. Such catalysts are metal complexes, which include metals selected from the group consisting of Rh, Co, Ir, Ru, Fe, Ni, Pd, Pt, Os, and mixtures thereof. Particularly preferred are complexes of Rh, Co, Pd, and Ru, with Co being particularly preferred. Preferred non-cobalt complexes include $Pd(CH_3CO_2)_2$, $PdCl_2(PPh_3)_2$, and $RhCl(CO)(PPh_3)_2$. Preferred cobalt complexes include $HCo(CO)_4$, $Co_2(CO)_8$, $Co_4(CO)_{12}$, and modified cobalt complexes represented by the general formula $[Co(CO)_3L]_2$ wherein L is a ligand such as trisubstituted phosphine (e.g. tributylphosphine, trioctylphosphine, tridecylphosphine, tribenzylphosphine) or organic nitrogen (e.g. pyridine, picoline, quinoline, lutidine, and pyrrolidone). Cobalt compounds such as cobalt carbonate, cobalt acetylacetonate, cobalt acetate and cobalt octanoate also give cobalt carbonyl complexes under the reaction conditions and act as cobalt carbonyl catalyst species. Consequently, when these cobalt compounds are fed to the reaction vessel, substantially the same effect as that of feeding cobalt carbonyl complexes can be produced.

The fluid compositions of this invention can further contain acetals. These acetals are represented by a compound of the formula III:

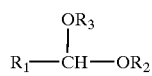

wherein $R_1$ is $C_3$–$C_6$ alkyl, $R_2$ is $C_1$–$C_4$ alkyl, and $R_3$ is $C_1$–$C_4$ alkyl. Desirably, the compound of formula III is present in the fluid compositions at not greater than a concentration of about 5 wt. %, preferably about 0.01 wt. % to about 3 wt. %, more preferably about 0.05 wt. % to about 2 wt. %.

The hydroesterification reaction is carried out in a reaction vessel equipped with a stirrer or in a columnar reaction vessel. The reaction can be either continuous or batch. It is also possible to provide a separate vessel for catalyst preparation, synthesize therein a metal complex from the above-mentioned metal compounds in a conventional manner, and feed the liquid reaction mixture as is to the hydroesterification reaction vessel.

The concentration of the catalyst in the reaction system is generally in the range of 0.0001 to 0.1 mole per mole of the olefinic compound charged, depending upon the reaction conditions, kind of the catalyst, presence or absence of (excess) ligand, and so forth. When a modified cobalt catalyst is used for the carbonylation, the amount of the ligand is preferably about 0.5 to 5 moles per gram atom of cobalt.

The reaction is generally carried out in an organic solvent in the presence of the catalyst. The organic solvent to be used in the hydroesterification reaction of the invention preferably dissolves the carbonylation catalyst, yet does not adversely affect the reaction. Preferably, the starting olefinic compound, the products, and certain of the byproducts, alone or in combination, serve as the reaction solvent. Other examples of the reaction solvent include aromatic hydrocarbons such as benzene, toluene, xylene and dodecylbenzene; alicyclic hydrocarbons such as cyclohexane; ethers such as dibutyl ether, ethylene glycol dimethyl ether, diethylene glycol diethyl ether, tetraethylene glycol dimethyl ether and tetrahydrofuran; and esters such as diethyl phthalate and dioctyl phthalate. In selecting the solvent, some physical constants, e.g. differences in boiling points among the starting material, reaction product and solvent should be taken into consideration.

Preferably, the combination of feed components (e.g., alkenes or alkene mix, CO, alcohol, and metal catalyst complex) are combined and reacted such that, upon separation of metal complex catalyst, little additional processing is needed. However, additional separation processing may be required to meet the desirable combination of branched and linear components, and to obtain the desirable characteristics. Separation may be by distillation, solvent extraction or adsorption of undesirable by products using molecular sieves, or by any other equivalent processing. Removal of undesired quantities of acid and moisture can be particularly accomplished by further treatment such as filtering the product with a filter aid or contacting with a molecular sieve.

Should it be necessary, dilution or other components can be added to the hydroesterification product to adjust the fluid compositions characteristics as well. Such additive components include:

(i) branched and/or straight chained $C_6$–$C_9$ alkanes;

(ii) $C_7^+$ aromatics;

(iii) $C_1$–$C_9$ alcohols (preferred alcohols include methanol, ethanol, n-propanol, isopropanol, n-butanol, isobutanol, tert-butanol, sec-butanol, n-pentanol and the like);

(iv) $C_3$–$C_9$ ketones (preferred ketones include acetone, methyl ethyl ketone, methyl isobutyl ketone and the like);

(v) $C_3$–$C_{12}$ esters (preferred esters include methyl acetate, tert-butyl acetate, methyl 1,1,1-trimethyl acetate, n-butyl acetate, n-pentyl acetate and the like);

(vi) $C_3$–$C_{12}$ ethers; and (vii) $C_1$–$C_{12}$ halocarbons.

The ester containing fluids of this composition exhibit at least one, preferably a combination of desirable performance characteristics of ozone formation potential (OFP), flash point, particle formation, evaporation rate, Hansen Solubility Parameter, viscosity, initial boiling point, water content, and total acid content. It is particularly desirable that the fluid compositions have any of two or more the desirable performance characteristics. In its most preferred form, the fluid compositions have all of these performance attributes.

The ozone formation potential of the fluid compositions of this invention can be determined by any scientifically recognized or peer reviewed method including but not limited to the $K^{OH}$ scale, the MIR scale, smog chamber studies, and modeling studies such as those performed by Dr. William P. L. Carter. The $K^{OH}$ scale is documented in, for example, Picquet et al., *Inat. J. Chem. Kinet.* 30, 839–847 (1998); Bilde et al.,*J. Phys. Chem. A* 101, 3514–3525 (1997). It is preferred, however, that the Absolute Maximum Incremental Reactivity (MIR) scale, measured in grams ozone produced/gram of fluid compositions, be used. A list of compounds and their MIR values is available in the Preliminary Report to California Air Resources Board. Contract No. 95-308, William P. L. Carter, Aug. 6, 1998, the list being incorporated herein by reference. See also CARB, "Proposed Reactivity Adjustment Factors for Transitional Low Emissions Vehicles—Staff Report and Technical Support Document," California Air Resources Board, Sacramento, Calif., Sep. 27, 1991, which is incorporated herein by reference. A table of known MIR values may be found on the Internet through links at the site http://helium.ucr.edu/~carter/index.html, see in particular http://www.cert.ucr.edu/~carter/r98tab.htm, the details of which are incorporated herein by reference. A detailed explanation of the methods employed and the determination of incremental reactivities and MIR scale may be found in the literature. See for instance, *International Journal of Chemical Kinetics,* 28 497–530 (1996); *Atmospheric Environment.* 29 2513–2527 (1995), and 29, 2499–2511 (1995); and *Journal of the Air and Waste Management Association*, 44, 881–899 (1994); *Environ. Sci. Technol* 23. 864 (1989). Moreover, various computer programs to assist in calculating MIR values are available, such as the SAPRC97 model, at http://helium.ucr.edu/~carter/saprc97.html.

The MIR of the fluid compositions of this invention is preferably less than or equal to 2.0 gram of ozone produced per gram of fluid compositions, more preferably less than or equal to 1.5 gram of ozone produced per gram of fluid compositions, and most preferably less than or equal to 1.0 gram of ozone produced per gram of fluid compositions. The benefits of the invention in reducing ozone formation can be achieved by replacing a first fluid with a second fluid, in whole or in part, wherein the MIR of the second fluid is reduced from that of the first fluid, even if the second fluid has an MIR greater than 2.0 gram of ozone produced per gram of fluid compositions.

The flash point of the compositions of this invention is desirably at least 3° C., preferably greater than 7° C., more preferably greater than 14° C., most preferably greater than 21° C. One of ordinary skill in the art can readily determine the flash point of the composition using known methods such as ASTM D92-78.

The evaporation rate should be suitable for the intended purpose. In many if not most applications, the fluid according to the invention will be used to replace, at least in part, a fluid which has a reactivity in ozone formation greater than 2.0 in Absolute MIR units. It is convenient for the fluid of this invention to have an evaporation rate less than 12 times the evaporation rate of n-butyl acetate, preferably in a range of 0.1 to 12 relative to n-butyl acetate, and more preferably in a range of 0.5 to 8. Evaporation rates may also be given relative to n-butyl acetate at 1.0 (ASTM D3539-87). Ranges of evaporation rates important for different applications are 5-3, 3-2, 2-1, 1.0-0.3, 0.3-0.1, and <0.1, relative to n-butyl acetate at 1.0.

The fluid compositions of this invention can be used as a solvent for resin type materials in general. A product which comprises the solvent and resin materials exhibits acceptable shelf life as demonstrated by low particle formation. Desirably, the fluid compositions with the added resin, such as for example an alkali-soluble resin, will have not greater than 500 particles of at least 15 μm in diameter, measured after one month storage at 40° C. Preferably, the fluid compositions will have no more than 250 particles of at least 15 μm in diameter, more preferably no more than 100 particles of at least 15 μm in diameter, measured under the same conditions. The particles are preferably measured using an automatic fine-particle measurement tester manufactured by HIAC/ROYCO.

Particle counting is described in greater detail in U.S. Pat. No. 5,405,720, the details of which are incorporated herein by reference.

The fluid compositions of the invention are preferably used as a solvent. The solvent may act in the traditional manner of a solvent by dissolving completely the intended solute or it may act to disperse the solute. It is important that the solvency of the fluid be adequate for the intended purpose. For purposes of this invention, the solvency is determined according to Hansen Solubility Parameters.

A description of Hansen Parameters is found on the Internet at http://palimpsest.stanford.edu/byauth/burke/solpar/solpar6.html, the details of which are incorporated herein by reference. In part this source states that the most widely accepted three component system is the three parameter system developed by Charles M. Hansen in 1966. Hansen parameters divide the total into three parts: a dispersion force component ($\delta_d$). a hydrogen bonding component ($\delta_h$), and a polar component ($\delta_p$). The components are additive. The dispersion force for a particular liquid is calculated using the homomorph method where the homomorph of a polar molecule is the nonpolar molecule most closely resembling it in size and stricture (n-butane is the homomorph of n-butyl alcohol). The Hildebrand value for the nonpolar homomorph (being entirely due to dispersion forces) is assigned to the polar molecule as its dispersion component value. This dispersion value (squared) is then subtracted from the Hildebrand value (squared) of the liquid the remainder is the value representing the total polar interaction of the molecule ($\delta_a$). Through trial and error experimentation on numerous solvents and polymers, Hansen separated the polar value into polar and hydrogen bonding component parameters best reflecting empirical evidence. For further description of Hansen Solubility Parameters, see Industrial Solvents Handbook by Wesley Archer, 1996, Marcel Dekker, the pertinent portions of which are incorporated herein by reference, particularly pages 35–68 and-297–309.

Preferably, the fluid compositions of this invention have Hansen Solubility Parameters of $\delta_d$ between about 13 to 20, $\delta_p$ of between about 2 to 10, and $\delta_h$ of between about 3 to 18. The Hansen Solubility Parameters of the fluid compositions of this invention can be varied within the preferred boundary ranges by the addition of other solvents as long as the appropriate balance of the esters of formula I is maintained.

The viscosity of the fluid compositions of this invention should be of a viscosity to enable facile application. The viscosity of the fluid should be chosen in a coatings application such that the fluid carries the polymer to the surface being coated with a viscosity which enables ready application, and then evaporates at a rate which is chosen to avoid sagging, peeling or extensive time to dry. The viscosity of the fluid compositions then is dependent on the fluid concentration, application temperature, baking conditions, polymer, etc.

The initial boiling point of the fluid compositions of this invention should be sufficiently low to ensure desirable evaporation, yet sufficiently high to sufficiently maintain in the fluid state at ambient conditions. Preferably the initial boiling point of the fluid is at least about 60° C., more preferably at least about 70° C., most preferably at least about 80° C.

The fluid compositions of this invention are desirably low in water and total acid content. The lower the water and total acid content, the greater the stability of the compounds of formula I and formula II. It is preferred that the fluid compositions have a moisture content of less than or equal to about 0.5 wt. %, more preferably less than or equal to about 0.3 wt. %, most preferably less than or equal to about 0.1 wt. %. Water content is preferably measured by ASTM method E-1064-92, Standard Test Method for Water in Organic Liquids by Coulometric Karl Fischer Titration.

It is preferred that the fluid compositions of the invention have a total acid content of less than or equal to about 0.1 wt. %, more preferably less than or equal to about 0.05 wt. %, most preferably less than or equal to about 0.01 wt. %. Total acid content is preferably measured by ASTM method D 1613-96, Standard Test Method for Acidity in Volatile Solvents and Chemical Intermediates Used in Paint, Varnish, Lacquer and Related Products.

The fluid compositions of this invention are preferably low in toxicity. One way to measure the toxicity is to measure the dose-effect relationship on a living organism. The dose is preferably measured in mg of fluid compositions per kg of body mass. This is preferably done experimentally by administering the fluid compositions to mice or rats at several doses in the lethal range and plotting the logarithm of the dose versus the percentage of the population killed by the composition. The dose lethal to 50% of the test population is called the median lethal dose ($LD_{50}$) and is typically used as a guide for the toxicity. See, for instance, Kirk-Othmer Encyclopedia of Chemical Technology, Fourth Edition, Vol. 24, pp. 456–490. Currently an $LD_{50}$ of >500 mg/kg qualifies as "not classified" for oral toxicity under OSHA rules. EU (European Union) uses a cutoff of >2,000 mg/kg. It is preferred that the fluid or fluid blend according to the invention have an oral rat $LD_{50}$ of >500 mg/kg, more preferably >1000 mg/kg, still more preferably >2,000 mg/kg, even more preferably >3,000 mg/kg, and most preferably >5,000 mg/kg. Likewise, the fluid compositions should not be problematic by dermal or inhalation routes and should also not be an eye or skin irritant, as measured by OSHA or European Union (EU) standards.

The invention provides fluid compositions which preferably produce reduced ozone formation due to atmospheric photochemical reactions, thereby avoiding the deficiencies associated with halogenated organic compounds, particularly toxicity, ozone depletion, incineration by-products and waste disposal problems. In this aspect, the volatile components of the preferred fluid solvents and fluid solvent blends preferably do not have more than 2.0 wt. % of halogen and more preferably less than 0.5 wt. %, and most preferably less than 0.1 wt. %.

The fluid according to the invention should be inert and thermally stable so that it does not break down. For instance, the material should not break down into reactive species. In a preferred embodiment, the fluid is more thermally stable than tert-butyl acetate.

The fluid compositions according to the invention may be used in any process using a fluid, and particularly those processes wherein at least a portion of the fluid evaporates and even more particularly wherein at least a portion evaporates into the atmosphere. Preferred processes are those utilizing the fluid as one or more of a carrier, diluent, dispersant, solvent, and the like, including processes wherein the fluid functions as an inert reaction medium in which other compounds react; as a heat-transfer fluid removing heat of reaction; to improve workability of a manufacturing process; as a viscosity reducer to thin coatings; as an extraction fluid to separate one material from another; as a tackifier or to improve adhesion to a substrate for better bonding; as a dissolving medium to prepare solutions of polymers, resins, and other substances; to suspend or disperse pigments and other particulates; and the like.

It is preferred that the process be a stationary process and also preferred that the process be a non-combustion process. It is particularly beneficial if the fluid according to the invention be used to replace at least a portion of a traditional industrial solvent in a process using a large amount of fluid, e.g., a process using 1000 lb./year (500 kg/year), even more preferably 5 tons/year (5000 kg/yr.), still more preferably 50 tons/year (50,000 kg/yr.), and most preferably one million lbs./year (500,000 kg/yr.).

It is also preferred that the process in which a fluid or blend according to the invention is used or in which at least one fluid according to the invention replaces, at least partially, a fluid having a higher MIR, be a process in which the fluid is intended to evaporate, such as in a coating process. In such a process where the fluid is intended to evaporate, it is preferred that at least 10% of the fluid or fluids evaporate, more preferably 20% of the fluids, and so on, so that it is most preferable if >99% of the fluid or fluids present in the coating evaporate.

Furthermore, one of the greatest environmental benefits of replacing a currently-used industrial solvent with a solvent according to the invention will be realized if performed in a geographic area where monitoring for ozone and particulate matter formation occurs, and more particularly in geographic areas defined by a city and its contiguous area populated by at least 500,000 persons, and wherein the replacement of at least a portion of the currently-used industrial solvent with a fluid according to the invention causes a reduction in the ozone formation, as measured by either monitoring devices or by a calculation of the reduction using the MIR of the industrial solvent replaced and the fluid added according to the present formation.

The invention offers fluid compositions for use in a variety of industrial applications such as paints and other coatings, adhesives, sealants, agricultural chemicals, cleaning solution, consumer products such as cosmetics, pharmaceuticals, drilling muds, extraction, reaction diluents, inks, metalworking fluids, photoresists, etc.

The most preferred use of the fluids according to the invention is with any process wherein the reduction of ozone formation is desired, and more particularly in consumer products, and coatings such as auto refinishing, architectural and industrial coatings and paints.

Paints and coatings comprise the largest single category of traditional solvent consumption, accounting for nearly half the solvents used. Fluids serve multiple functions in paints and coatings, including solubility, wetting, viscosity reduction, adhesion promotion, and gloss enhancement. Fluids dissolve the resins, dyes and pigments used in the coating formulations. Also, prior to application, it is common practice to add a solvent thinner to attain the desired viscosity for the particular application. Solvents begin to evaporate as soon as the coating materials are applied. As the solvent evaporates, film formation occurs and a continuous, compact film develops. Single solvents are sometimes used in coatings formulations, but most formulations are blends of several solvents. In many coatings applications, the solvent system includes a slow-evaporating active solvent that remains in the film for an extended period to enhance the film's gloss and smoothness. Because of evaporation and the large amounts of solvents used in coatings, there is a significant amount of VOC emissions into the atmosphere.

Resins which may be incorporated into compositions comprising fluids according to the invention include acrylic, alkyd, polyester, epoxy, silicone, cellulosic and derivatives thereof (e.g., nitrocellulosic and cellulosic esters), PVC, and isocyanate-based resins. Numerous pigments may also be incorporated into compositions according to the invention, and it is within the skill of the ordinary artisan to determine proper selection of the resin and pigment, depending on the end use of the coating.

One cleaning application is cold solvent cleaning which is used to degrease metal parts and other objects in many operations. Mineral spirits have been popular in cold cleaning, but are being supplanted by higher flash point hydrocarbon solvents due to emissions and flammability concerns. Efforts to eliminate organic solvents entirely from cleaning compositions have not been successful because aqueous cleaners do not have the performance properties that make organic solvent based cleaners so desirable. This invention allows formulators the option to seek the use of solvents with very low reactivity as environmentally preferred products meeting environmental concerns and customer performance concerns.

A cleaning solution application that uses evaporation to clean is called vapor degreasing. In vapor degreasing, the solvents vaporize and the cold part is suspended in the vapor stream. The solvent condenses on the part, and the liquid dissolves and flushes dirt, grease, and other contaminants off the surface. The part remains in the vapor until it is heated to the vapor temperature. Drying is almost immediate when the part is removed and solvent residues are not a problem. The most common solvent used in vapor degreasing operations has been 1,1, 1-trichloroethane. However, since 1,1,1-trichloroethane is being phased out due to ozone depletion in the stratosphere, alternatives are needed. Moreover, chlorine-based solvents have toxicity concerns. Thus, some of the low reactivity, high flash point solvents in this invention can be used in place of 1,1,1-trichloroethane and other halogenated solvents.

An application that is similar to coatings is printing inks. In printing inks, the resin is dissolved in the solvent to produce the ink. Most printing operations use fast evaporating solvents for best production speeds, but the currently used solvents are highly reactive. Some of the previously described fast evaporation, high flash point, low reactivity in ozone formation fluids according to the invention are suitable for printing inks.

An application that is suitable to the low toxicity, high flash point and low reactivity in ozone formation fluids according to the invention is agricultural products. Pesticides are frequently applied as emulsifiable concentrates. The active insecticide or herbicide is dissolved in a solvent, which also contains an emulsifier. Solvent selection is critical for this application. It can seriously impact the efficiency of the formulation. The solvent should have adequate solvency for the pesticide, promote good dispersion when diluted with water, have low toxicity and a flash point high enough to minimize flammability hazards.

Extraction processes, used for separating one substance from another, are commonly employed in the pharmaceutical and food processing industries. Oilseed extraction is a widely used extraction process. Extraction-grade hexane is a common solvent used to extract oil from soybeans, cottonseed, corn, peanuts, and other oil seeds to produce edible oils and meal used for animal feed supplements. Low toxicity, high flash point, low MIR fluids and fluid blends of the invention can be useful in such industries.

The fluid compositions of this invention can be used as a solvent for various positive or negative type photoresists. Such compositions comprise an alkali-soluble resin, a radiation sensitive resin, and the fluid compositions of this invention. In this use, the fluid is a solvent for the combination of the alkali-soluble resin and the radiation sensitive resin. Typical alkali-soluble resins include alkali-soluble novolaks, polyhydroxy-styrenes and their derivatives, styrene-maleic anhydride copolymers, polyvinyl hydroxybenzoates, carboxyl group-containing methacrylate resins, and combinations thereof. Typical radiation sensitive resins include 1,2-quinonediazide compounds and azide compounds. Preferred are 1,2-quinonediazide acid esters of polyhydroxy compounds having at least 3 hydroxyl groups, preferably 4 hydroxyl groups.

In addition to the above-mentioned applications, other applications that can use high flash point, low toxicity, low reactivity in ozone formation fluids are adhesives, sealants, cosmetics, drilling muds, reaction diluents, metal working fluids, and consumer products, such as pharmaceuticals or cosmetics.

This invention will be better understood with reference to the following examples, which are intended to illustrate specific embodiments within the overall scope of the invention as claimed.

EXAMPLE 1

In a continuous pilot plant high pressure reactor, multiple runs were made contacting a raffinate-2 stream with CO, methanol, and a cobalt carbonylation catalyst using a variety of ligands. The reaction conditions, types of ligands, and results of the reactions are shown in Table 1.

TABLE 1

Carbonylation of Raffinate-2 stream With Methanol
T = 150° C.; L/Co = 17; Methanol/Olefin Stream = 2.0;
$P_{total}$ = 2100 psig; Olefin Stream/Co = 100; H2 in gas = 3.5%

| Run No. | Ligand | Total Run Time (min.) | Butene Conversion (Mol. %) | Selectivity to $C_6$ Ester* | Normal/ Iso |
|---|---|---|---|---|---|
| 1 | 3-Picoline | 165 | 84 | 96.5 | 4.7 |
| 2 | 4-Ethyl-Pyridine | 180 | 67 | 96.6 | 4.6 |
| 3 | 3,4-Lutidine | 219 | 33.5 | 94.4 | 4.5 |
| 4 | iso-Quinoline | 189 | 42.9 | 78.8 | 5.0 |
| 5 | N-Methyl-Pyrrolidone | 180 | 51.8 | 90.4 | 2.1 |

*based on converted butenes

Table 1 demonstrates that the ester base component of the fluid compositions of this invention can be made in a one step hydroisomerization process using dilute alkene feed.

EXAMPLE 2

The product of Example 1 was distilled to separate the normal from the iso ester (>98% methyl n-pentanoate). This distilled product was evaluated against n-butyl acetate, a composition having a wide variety of fluid uses, but which has relatively poor environmental characteristics, for various performance characteristics. The results are shown in Table 2.

TABLE 2

Comparison of Physical Properties

| Property | Units | n-Butyl Acetate | Example 1 Product |
|---|---|---|---|
| Distillation | ° C. | | |
| IBP | | 126 | 127 |
| 5% | | 127 | 129 |
| 50% | | 127 | 129 |
| 95% | | 128 | 129 |
| DP | | 128 | 129 |
| Flash Point by TAG | ° C. | 27.0 | 27.5 |
| Viscosity at 25° C. | cSt | 0.79 | 0.8 |
| Pour Point | ° C. | <−42 | <−42 |

The results shown in Table 2 demonstrate that the compounds of formula I have substantially the same characteristics as n-butyl acetate. This means that the compounds of formula I as an environmentally friendly substitute for n-butyl acetate. The blend of the normal and iso esters from example 1 (i.e., without distillation) are expected to exhibit similar results.

Having now fully described this invention, it will be appreciated by those skilled in the art that the invention can be performed within a wide range of parameters within what is claimed, without departing from the spirit and scope of the invention.

What is claimed is:

1. A method of making a fluid composition, comprising: contacting a mixture of a raffinate-1 stream or a raffinate-2 stream, CO, and $C_1$–$C_4$ alkanol with a carbonylation catalyst to provide a composition containing:
   (a) a compound of formula I:

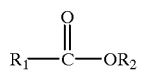

wherein $R_1$ is linear $C_3$–$C_6$ alkyl, and $R_2$ is $C_1$–$C_4$ alkyl;
   (b) a compound of formula II:

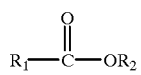

wherein $R_1$ is branched $C_3$–$C_6$ alkyl, and $R_2$ is $C_1$–$C_4$ alkyl; and $R_1$ of formula I and $R_1$ of formula II have an equal number of carbons, with formula I and formula II being present at a weight ratio of 2–100:1; and
   (c) a compound of the formula III:

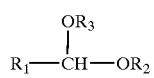

wherein $R_1$ is $C_3$–$C_6$ alkyl, $R_2$ is $C_1$–$C_4$ alkyl, and $R_3$ is $C_1$–$C_4$ alkyl.

2. The method of claim 1, wherein the composition has Hansen Solubility Parameters of $\delta_d$ between about 13 to 20, $\delta_p$ of between about 2 to 10, and $\delta_h$ of between about 3 to 18.

3. The method of claim 1, wherein the composition has an initial boiling point of at least about 70° C.

4. The method of claim 1, wherein the composition has a flash point of at least 3° C.

5. The method of claim 1, wherein the composition further comprises at least one additional compound selected from the group consisting of $C_6$–$C_9$ alkanes, $C_7^+$aromatics, $C_1$–$C_9$ alcohols, $C_3$–$C_9$ ketones, $C_3$–$C_{12}$ esters, $C_3$–$C_{12}$ ethers, and $C_1$–$C_{12}$ halocarbons.

6. The method of claim 1, wherein the composition has an evaporation rate of 0.1 to 12 relative to that of n-butyl acetate.

7. The method of claim 1, wherein the composition has a water content of less than or equal to about 0.5 wt. %.

8. The method of claim 1, wherein the composition has a total acid content of less than or equal to 0.1 wt. %.

9. The method of claim 1, wherein the compound of formula I and the compound of formula II is present in the fluid at a total concentration of at least 5 wt. %.

10. The method of claim 1, wherein $R_1$ of formula I and $R_1$ of formula II are $C_4$.

11. The method of claim 1, wherein $R_1$ of formula I and $R_1$ of formula II is $C_4$ and $R_2$ of formula I and $R_2$ of formula II is $C_1$.

12. The method of claim 1 where the fluid further comprises a compound of the formula III:

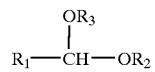

wherein $R_1$ is $C_3$–$C_6$ alkyl, $R_2$ is $C_1$–$C_4$ alkyl, and $R_3$ is $C_1$–$C_4$ alkyl.

13. The method of claim 12, wherein the compound of formula III is present in the fluid composition at not greater than a concentration of about 5 wt. %.

14. The method of claim 12, wherein the composition has an ozone forming potential less than or equal to 2.0 g. of ozone produced per g. of fluid.

15. The method of claim 12, wherein the composition has Hansen Solubility Parameters of $\delta_d$ between about 13 to 20, $\delta_p$ of between about 2 to 10, and $\delta_h$ of between about 3 to 18.

16. The method of claim 12, wherein the composition has an initial boiling point of at least about 70° C.

17. The method of claim 12, wherein the composition has a flash point of at least 3° C.

18. The method of claim 12, wherein the composition further comprises at least one additional compound selected from the group consisting of $C_6$–$C_9$ alkanes, $C_7^+$aromatics, $C_1$–$C_9$ alcohols, $C_3$–$C_9$ ketones, $C_3$–$C_{12}$ esters, $C_3$–$C_{12}$ ethers, and $C_1$–$C_{12}$ halocarbons.

19. The method of claim 12, wherein the composition has an evaporation rate of 0.1 to 12 relative to that of n-butyl acetate.

20. The method of claim 12, wherein the composition has a water content of less than or equal to about 0.5 wt. %.

21. The method of claim 12, wherein the composition has a total acid content of less than or equal to 0.1 wt. %.

22. The method of claim 12, wherein the compound of formula I and the compound of formula II are present in the fluid at a total concentration of at least 5 wt. %.

23. The method of claim 12, wherein $R_1$ of formula I and $R_1$ of formula II are $C_4$.

24. The method of claim 12, wherein $R_1$ of formula I and $R_1$ of formula II are $C_4$ and $R_2$ of formula I and $R_2$ of formula II are $C_1$.

* * * * *